US00PP08267P

United States Patent [19]

Meilland

[11] Patent Number: Plant 8,267

[45] Date of Patent: Jun. 22, 1993

[54] ROSE PLANT — MEIKISTER VARIETY

[75] Inventor: Alain A. Meilland, Antibes, France

[73] Assignee: The Conard-Pyle Company, West Grove, Pa.

[21] Appl. No.: 799,450

[22] Filed: Nov. 26, 1991

[30] Foreign Application Priority Data

Feb. 8, 1991 [NL] Netherlands ..... R001741

[51] Int. Cl.[5] ..... A01H 5/00

[52] U.S. Cl. ..... Plt./28

[58] Field of Search ..... Plt./22, 27, 28

[56] References Cited

U.S. PATENT DOCUMENTS

P.P. 7,334 9/1990 Meilland ..... Plt. 28

*Primary Examiner*—Howard J. Locker

*Attorney, Agent, or Firm*—Burns, Doane, Swecker & Mathis

[57] ABSTRACT

A new and distinct variety of Floribunda rose plant is provided which abundantly forms attractive semi-double blossoms commonly in the form of substantially uniform clusters which are long lasting when cut and placed in a vase. The blossoms are Rose Bengal suffused with Carmine Rose and are very stable in coloration. The plant exhibits vigorous vegetation and is semi-erect. The new variety is well adapted for greenhouse forcing and is particularly well suited for cut flower production. Good resistance to cryptogamic diseases also is exhibited.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) of the new variety was the Jeldaniran variety (U.S. Plant Pat. No. 5,636). The male parent (i.e., the pollen parent) of the new variety was the Sterling Silver variety (U.S. Plant Pat. No. 1,433). The parentage of the new variety can be summarized as follows:

Jeldaniran × Sterling Silver.

The seeds resulting from the above pollination were sown and 21 small plants were obtained which were physically and biologically different from each other. Selective study resulted in the identification of a single plant of the new variety.

It was found that the new variety of Floribunda rose plant of the present invention possesses the following combination of characteristics:

(a) forms in abundance attractive semi-double blossoms commonly borne in substantially uniform clusters which are Rose Bengal suffused with Carmine Rose and are long lasting when cut and placed in a vase,
(b) forms medium green adult wood,
(c) forms vigorous vegetation,
(d) is particularly well suited for cut flower production, and
(e) is not particularly affected by cryptogamic diseases.

The flower coloration has been found to be very stable. Also, the plant is well adapted for greenhouse forcing.

The new variety undergoes asexual propagation by a number of routes, including budding, grafting, cuttage, etc. The characteristics of the new variety have been found to be strictly transmissible by such asexual propagation from one generation to another in both France and the United States.

The new variety has been named the Meikister variety.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indica* understock and growing in greenhouses at Cap d'Antibes, France.

DETAILED DESCRIPTION

Figures 1, 2, 3, 4, 5, 6, 7, 8, 9, 10, 11, 12, 13, 14, 15, 16:
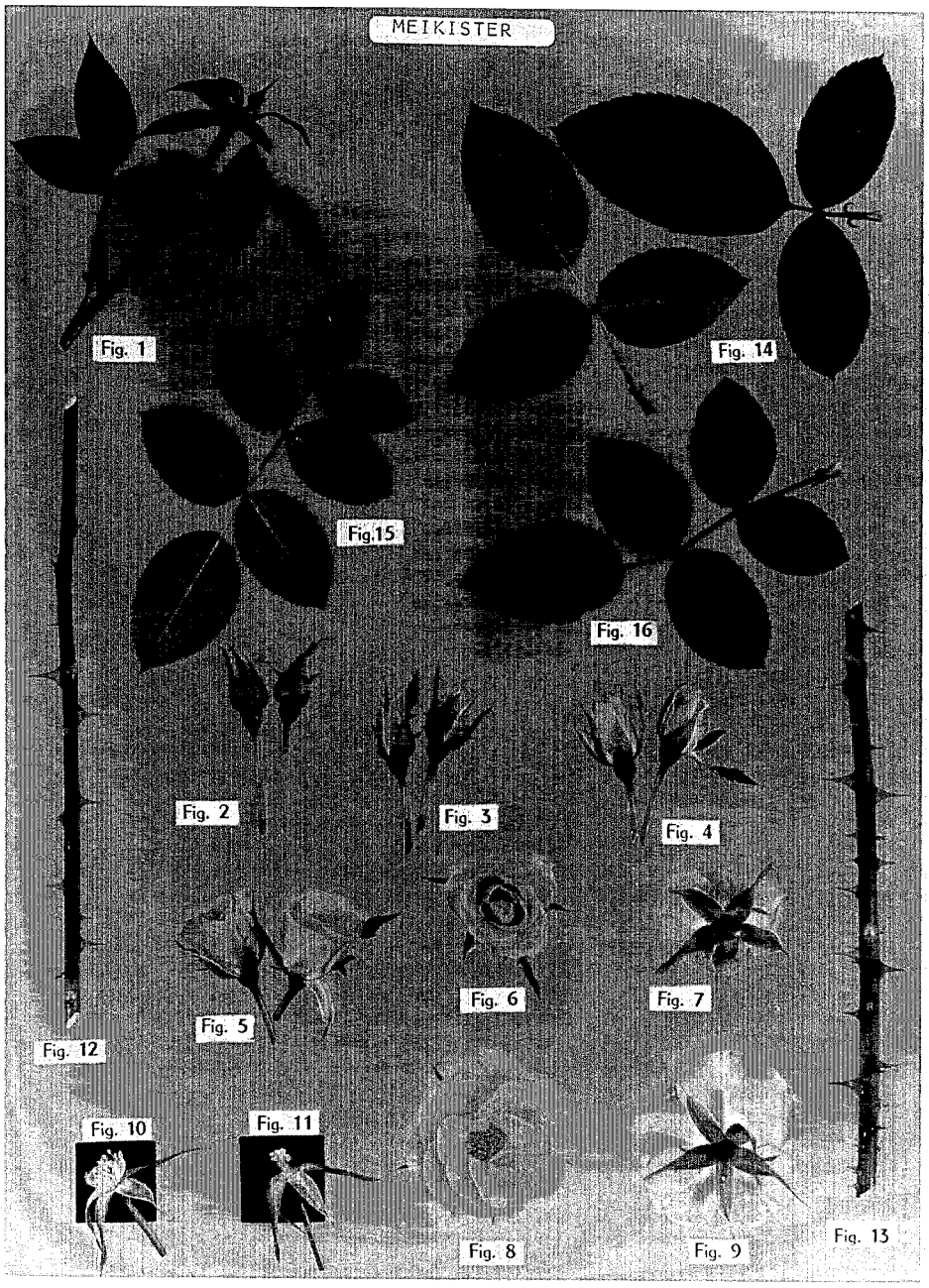
FIG. 1 illustrates a specimen of a young shoot.
FIG. 2 illustrates a specimen of a pair of floral buds before the opening of the sepals.
FIG. 3 illustrates a specimen of a pair of floral buds at the opening of the sepals.
FIG. 4 illustrates a specimen of a pair of floral buds at the opening of the petals.
FIG. 5 illustrates a specimen of a pair of flowers in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of an adult main branch.
FIG. 14 illustrates a specimen of a pair of leaves with three leaflets — under surface (left), and — upper surface (right)
FIG. 15 illustrates a specimen of a leaf with seven leaflets — under surface.
FIG. 16 illustrates a specimen of a leaf with five leaflets — upper surface.

The chart used in the identification of the colors is that of The Royal Horticultural Society (R.H.S. Colour Chart). The terminology which precedes reference to the chart has been added to indicate the corresponding color in more common terms. The description is based on two year old specimens of the new variety during November while budded on *Rosa indica* understock and growing in greenhouses at Cap d'Antibes, France.

Class: Floribunda.

Plant:

*Height.*—When the plants are cut to a height of 85 cm., the flowering stems commonly measure approximately 40 to 60 cm. When grown in fields at Wasco, Calif., the plants commonly achieve a height of approximately 90 cm. at the end of one growing season.

*Habit.*—Semi-erect.

Branches:

*Color.*—Young stems: lettuce green, Yellow-Green Group 144A, more or less stained with reddish coloration. Adult wood: medium green, Yellow-Green Group 146B.

*Thorns.*—Size: medium. Quantity: average. Color: pinkish on young stems, and greenish changing to light tan on mature wood.

Leaves:

*Stipules.*—Adnate, pectinate, fairly wide and linear.

*Petioles.*—Upper surface: striped reddish green on young foliage and medium green on mature foliage with more or less glandular edges. Under surface: light green, with a few prickles.

*Leaflets.* 13 Number 3, 5, and 7 (most often). Shape: elliptic. Serration: regular. Texture: consistent. General appearance: fairly dense, semi-matte foliage. Color (young foliage): Upper surface: dark green, Yellow-Green Group 147A, and more or less tinged with reddish coloration. Under surface: medium green, Yellow-Green Group 148B, and more or less tinged with reddish coloration. Color (adult foliage): Upper surface: dark green, Yellow-Green Group 147A. Under surface: medium green, Yellow-Green Group 148B.

Inflorescence:

*Number of flowers.*—Commonly in clusters of up to 12 blooms which frequently are substantially uniform in appearance.

*Peduncle.*—Medium green, smooth, and approximately 7 to 10 cm. in length on average.

*Sepals.*—Upper surface: tomentose and greenish in coloration. Under surface: light green, smooth, and the outer sepals commonly are more or less appendiculate and sometimes end with a foliar-like appendix.

*Buds.*—Shape: conical. Length: approximately 2 cm. on average. Size: large. Color upon opening: Upper surface: Rose Bengal, Red-Purple Group 57A, more or less widely suffused with Carmine Rose, Red Group 52A. Under surface: Rose Bengal, Red-Purple Group 63B, more or less widely suffused with Carmine Rose, Red Group 52A.

*Flower.*—Shape: cup-like semi-double. Diameter: approximately 5 to 6 cm. on average. Color (when opening begins): Upper surface: Rose Bengal, Red-Purple Group 57A, more or less widely suffused with Carmine Rose, Red Group 52A. Under surface: Rose Bengal, Red-Purple Group 63B, more or less widely suffused with Carmine Rose, Red Group 52A. Color (when blooming): Upper surface: medium Rose Bengal, Red-Purple Group 57B, more or less widely suffused with Carmine Rose, Red Group 52B. Under surface: light Rose Bengal, Red-Purple Group 61C, more or less widely suffused with Carmine Rose, Red Group 52B. Color (at end of opening): Upper surface: medium Rose Bengal, Red-Purple Group 57B, more or less widely suffused with Carmine Rose, Red Group 52B. Under surface: light Rose Bengal, Red-Purple Group 61C, more or less widely suffused with Carmine Rose, Red Group 52B. Fragrance: none. Lasting quality: long lasting blossoms when cut and placed in a vase. Petal drop: good. Petal number: approximately 15 to 17 on average. Petal texture: consistent. Petal shape: usually rounded. Stamen number: approximately 127 on average. Anthers: yellowish in coloration, located at substantially the same level as the stigma. Filaments: bear coloration of greenish straw, and are of irregular heights. Pistils: approximately 42 on average. Stigmas: straw-like. Styles: light fuschia in coloration. Receptacle: medium green, smooth, and in longitudinal section in the shape of a pear at the dehiscence of the anthers.

Development:

*Vegetation.*—Vigorous.

*Blooming.*—Abundant.

*Resistance to diseases.*—Good.

*Aptitude to be forced.*—Good.

I claim:

1. A new and distinct variety of Floribunda rose plant characterized by the following combination of characteristics:

(a) forms in abundance attractive semi-double blossoms commonly borne in substantially uniform clusters which are Rose Bengal suffused with Carmine Rose and are long lasting when cut and placed in vase, (b) forms medium green adult wood, (c) forms vigorous vegetation, (d) is particularly well suited for cut flower production, and (e) is not particularly affected by cryptogamic diseases; substantially as herein shown and described.

* * * * *

MEIKISTER